US006277390B1

(12) United States Patent
Schaffner

(10) Patent No.: US 6,277,390 B1
(45) Date of Patent: Aug. 21, 2001

(54) UHMW POLYETHYLENE FOR IMPLANTS

(75) Inventor: Silvio Schaffner, Basadingen (CH)

(73) Assignee: Sulzer Orthopaedie AG, Baar (CH)

( * ) Notice: Subject to any disclaimer, the term of this patent is extended or adjusted under 35 U.S.C. 154(b) by 0 days.

(21) Appl. No.: 09/406,049

(22) Filed: Sep. 27, 1999

(30) Foreign Application Priority Data

Oct. 21, 1998 (EP) .................................................. 98811048

(51) Int. Cl.$^7$ ....................................................... A61F 2/02
(52) U.S. Cl. .............................................................. 424/422
(58) Field of Search ..................................... 424/422, 423

(56) References Cited

U.S. PATENT DOCUMENTS 5,650,485   7/1997   Sun .

FOREIGN PATENT DOCUMENTS

| 221403 | 2/1986 | (CS) . |
| 0542108A2 | 5/1993 | (EP) . |
| 0613923A1 | 9/1994 | (EP) . |

*Primary Examiner*—Carlos Azpuru
(74) *Attorney, Agent, or Firm*—Townsend and Townsend and Crew LLP

(57) ABSTRACT

UHMW polyethylene for implants which are intended for a sterilization by means of γ rays or electron beams are doped with vitamin E during the manufacture, which binds off the free radicals faster than the oxygen from the surroundings after the irradiation and thus prevents an oxidation and aging of the implants. A starting material in powder form is wetted at its surface with a liquid which has a suitable amount of vitamin E in order to achieve a concentration K of vitamin E of $0.01\% < K < 1\%$ on the polyethylene particles. After the evaporation of the liquid the PE powder is compressed to blocks or processed to rods at temperatures around 180° C.–240° C. and pressures from 2–10 MPa.

12 Claims, 1 Drawing Sheet

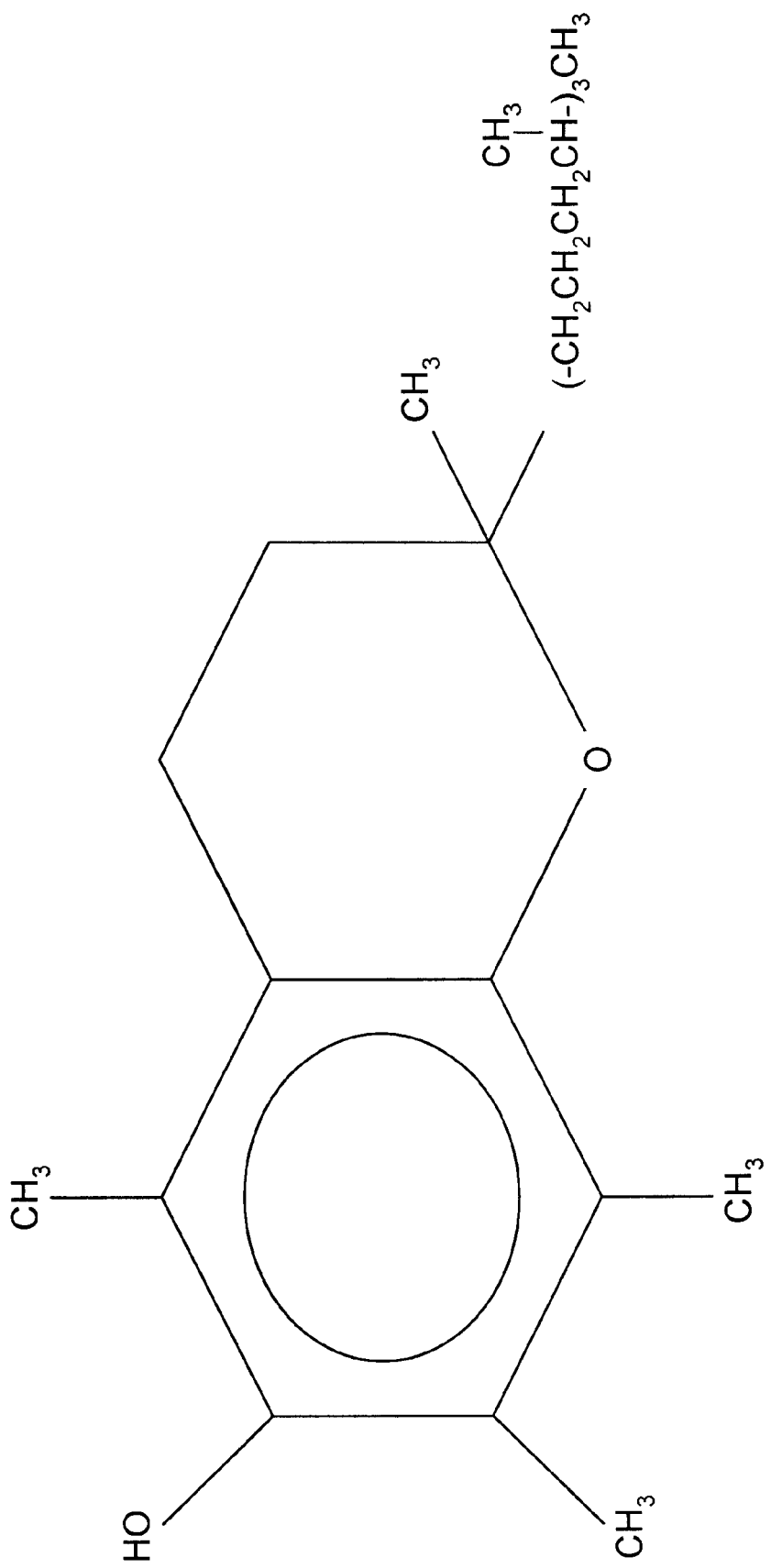
Figure 1. α-Tocopherol Structure Corresponding to Commercially Available Vitamin E

UHMW POLYETHYLENE FOR IMPLANTS

BACKGROUND OF THE INVENTION

The present invention is generally related to the manufacture of implants for medical purposes. More specifically, the present invention provides an implant made of UHMW polyethylene, intended for sterilization by means of γ rays or electron beams, which is manufactured in a way that inhibits oxidation, thus diminishing the implant's susceptibility to long-term brittleness and preventing increased wear at contact locations.

Only a few companies have specialized in the manufacture of UHMW polyethylene for medical purposes. A usual manufacture process uses a powder or a granulate which, at temperatures around 180° C.–240° C. and pressures around 2–10 MPa, is compressed into finished parts or extruded into blocks or bars from which implant parts (e.g., bearing shells of artificial hip joints or artificial knee joints) are manufactured.

A further processing step that is common in the manufacture of implant parts consists of welding the parts in a protective gas atmosphere (e.g., nitrogen), placing the implants into bags and sterilizing the implants in such bags via irradiation with γ rays or electron beams. Once sterilized, the implant parts can be stored and be readily available for use.

However, γ ray or electron beam irradiation not only sterilizes the implant part, but causes chain structures with free radicals to arise in the polyethylene, which leads to cross linking and/or oxidation in the presence of oxygen atoms. Oxygen is present in the polyethylene and can also diffuse slowly into the polyethylene, which causes the material to become brittle after several years, which reduces the mechanical properties of the implant and leads to increased wear.

Prior art has reported the stabilization of polyolefins against thermal oxidation and photo-oxidation which is not damaging to health. Such art shows various polyolefins age more slowly under natural environmental conditions if a tocopherol is mixed with them during the manufacturing process. In contrast to other antioxidants, such as derivatives of phenolamines and phosphides, which can be hazardous to health, it has been proposed that tocopherol be mixed with polyolefins, which are used in the food industry, health services or as implants, in order to achieve slower aging. Reports show that weight proportions of 0.01% to 5% of tocopherol in the polyolefins slow the thermal oxidation during the manufacture of the material and the photo-oxidation of the material under natural environmental conditions.

In light of the above, it would be desirable to provide implants made of UHMW polyethylene, and sterilized by means of irradiation with γ rays or electron beams, which had oxidation inhibiting characteristics, thus increasing the useful life of the implant.

SUMMARY OF THE INVENTION

The present invention generally provides an improved UHMW polyethylene material, and method for its manufacture, for use in the manufacture of implants meant to be sterilized via irradiation with γ rays or electron beams. In particular, the present invention provides a UHMW polyethylene material that inhibits the oxidation of the implant material, thus providing a more durable implant.

Specifically, the present invention uses a process wherein vitamin E is dispersely embedded in the polyethylene during the manufacture of implants. When the implants are irradiated for sterilization using γ rays or electron beams, the free radicals present are saturated more rapidly by vitamin E than by oxygen, thus preventing the early oxidation and aging of the implant. Thus, the present invention extends the life of the implant.

BRIEF DESCRIPTION OF THE DRAWINGS

FIG. 1 is a schematic illustration of the α-tocopherol structure corresponding to commercially available vitamin E.

DESCRIPTION OF THE SPECIFIC EMBODIMENTS

The present invention generally inhibits oxidation in implant parts which are irradiated with γ-rays or electron beams. This objective is accomplished by dispersely embedding vitamin E in the polyethylene with a concentration K of $0.01\% < K < 1\%$ to prevent UHMW polyethylene implants from becoming brittle in the long term and thereby wear at contact locations. Dispersely distributed vitamin E saturates the free radicals present following irradiation more rapidly than oxygen which has diffused through the polyethylene, and thus inhibits oxidation. Oxidation can be noticeably impaired at a percentage of vitamin E which is greater than 0.01%. However, too great a percentage of embedded vitamin E in the polyethylene, for example above 1%, leads to a worsening of the mechanical properties of the implant in that the Young's modulus, the tensile strength, and the notched bar impact value of the material worsen. Thus, the end objective is to perform a disperse distribution of vitamin E as uniformly as possible and with a cost and complexity which can be justified economically.

Further refinements in the invention can be obtained by uniformly producing smaller polyethylene particles and doping them uniformly at their surface with vitamin E, which can lead to more narrow and effective achievable limits for the average concentration of vitamin E. Such concentration K can amount to $0.1\% < K < 0.4\%$. Further, an improved selection and wetting of the polyethylene particles can lead to a vitamin E concentration K of $0.1\% < K < 0.2\%$.

Very small particles of UHMW polyethylene have a relatively large surface area in proportion to their volume. If one succeeds in grinding these particles very finely, which is possible with ultrasonic grinders which can produce the smallest particle sizes with crossing sound fronts, then vitamin E which is held in suspension in a liquid or otherwise contained in a solvent, can be deposited in a small and manageable concentration with the liquid on the polyethylene particles. The more similar the polyethylene particles are in diameter, the more similar is also their factor for the ratio of surface area to volume and the certainty, at a specific surface tension of the liquid, of depositing the same amounts of vitamin E on the particles when the liquid is evaporated, which is also possible at low temperatures in a vacuum. For example, alcohols are suitable solvents for vitamin E.

A fine powder which has arisen in the manner described above and which is uniformly doped with a low concentration of vitamin E can then be compressed into compact blocks and bars in a neutral atmosphere immediately or after an intermediate storage. The vitamin E is thus dispersely embedded in the blocks and bars and only fulfills its function when the finished processed implant parts have been irradiated for sterilization. The free radicals which are still present after irradiation are saturated more rapidly by the vitamin E than by the oxygen and thus early oxidation and aging is prevented.

Along with the main constituent α-tocopherol, natural vitamin E also contains β-tocopherol and further isomers which have a somewhat lesser effect as antioxidants. FIG. 1 illustrates the α-tocopherol structure corresponding to commercially available vitamin E in the form of a pasty mass which is soluble in organic solvents such as alcohols, ketones, and liquid alkanes such as ethanol, acetone or n-heptane. In determining the concentration and amount of the solution, the surface area of the polyethylene particles and that of the mixing vessel must be taken into account in order to wet the polyethylene particles with solvent and with vitamin E uniformly and in a concentration K of vitamin E which corresponds to their volume. The evaporation of the solvent can be carried out in an autoclave through the maintaining of a vacuum.

In order to safeguard against undesired reactions of the vitamin E, which is distributed over a large surface, the polyethylene particles, which are covered with vitamin E, can be stored in a vacuum or in a protective gas atmosphere.

What is claimed is:

1. An Implant made of UHMW polyethylene, where the implant has been machined out of UHMW polyethylene blocks or extruded rods, wherein vitamin E is dispersely imbedded in the polyethylene with a concentration K of 0.01%<K<1%, the implant being exposed within a protective gas atmosphere to γ ray or electron beam irradiation amounts of at least 2.5 Mrad to prevent the implant from becoming brittle in the long term and thereby wear and tear at contact locations.

2. A method for the manufacture of UHMW polyethylene for implants, where the implants have been machined out of UHMW polyethylene blocks or extruded rods, wherein vitamin E is dispersely imbedded in the polyethylene with a concentration K of 0.01%<K<1%, the implant being exposed within a protective gas atmosphere to γ ray or electron beam irradiation amounts of at least 2.5 Mrad to prevent the implant from becoming brittle in the long term and thereby wear and tear at contact locations, the method comprising:

mixing a powder or granulate of UHMW polyethylene with a liquid that contains vitamin E in a predetermined amount;

evaporating the liquid in order to deposit the vitamin E in a predetermined concentration on the polyethylene particles; and compressing the polyethylene particles into blocks at temperatures in a range of approximately 180° C.–240° C. and pressures in a range of approximately 2–10 MPa.

3. A method for the manufacture of UHMW polyethylene for implants, where the implants have been machined out of UHMW polyethylene blocks or extruded rods, wherein vitamin E is dispersely imbedded in the polyethylene with a concentration K of 0.01%<K<1%, the implant being exposed within a protective gas atmosphere to γ ray or electron beam irradiation amounts of at least 2.5 Mrad to prevent the implant from becoming brittle in the long term and thereby wear and tear at contact locations, the method comprising:

mixing a powder or granulate of UHMW polyethylene with a liquid that contains vitamin E in a predetermined amount;

evaporating the liquid in order to deposit the vitamin E in a predetermined concentration on the polyethylene particles; and extruding the polyethylene particles into rods at temperatures in a range of approximately 180° C.–240° C. and pressures in a range of approximately 2–10 MPa.

4. A method in accordance with claim 9 wherein the liquid consists of alcohol.

5. An implant made of UHMW polyethylene in accordance with claim 1, wherein the average concentration K of vitamin E amounts to 0.1%<K<0.4%.

6. An implant made of UHMW polyethylene in accordance with claim 1, wherein the average concentration K of vitamin E amounts to 0.1%<K<0.2%.

7. An Implant made of UHMW polyethylene in accordance with claim 1, wherein the vitamin E is α-tocopherol with a structure formula

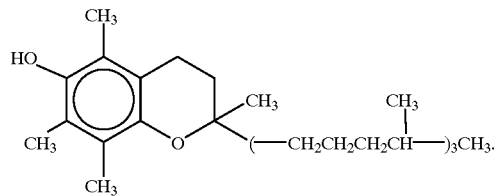

8. A Method in accordance with claim 2, wherein the particles of UHMW polyethylene have approximately the same size, at a specific ratio of surface area to volume, in order to deposit a predetermined concentration of vitamin E on all particles.

9. A Method in accordance with claim 2, wherein the liquid is a solvent for vitamin E.

10. A Method in accordance with claim 2, wherein the liquid is a carrier liquid in which vitamin E is embedded by way of suspension.

11. A Method in accordance with claim 2, wherein individual steps are carried out in a protective gas atmosphere without oxygen.

12. A Method in accordance with claim 2, wherein storage in a protective gas atmosphere is carried out between the second and the third step.

* * * * *

UNITED STATES PATENT AND TRADEMARK OFFICE
CERTIFICATE OF CORRECTION

| | | |
|---|---|---|
| PATENT NO. | : 6,277,390 B1 | Page 1 of 1 |
| APPLICATION NO. | : 09/406049 | |
| DATED | : August 21, 2001 | |
| INVENTOR(S) | : Schaffner et al. | |

It is certified that error appears in the above-identified patent and that said Letters Patent is hereby corrected as shown below:

On the Title Page,
Under Item (75), Inventors Add --Klaus Lederer-- and

Item (12) change "Schaffner" to --Schaffner et al.--

Signed and Sealed this

Twenty-fourth Day of October, 2006

JON W. DUDAS
*Director of the United States Patent and Trademark Office*